United States Patent
Kumar et al.

(10) Patent No.: US 9,936,880 B2
(45) Date of Patent: Apr. 10, 2018

(54) CAMERA BASED PHOTOPLETHYSMOGRAM ESTIMATION

(71) Applicant: William Marsh Rice University, Houston, TX (US)

(72) Inventors: Mayank Kumar, Houston, TX (US); Ashok Veeraraghavan, Houston, TX (US); Ashutosh Sabharwal, Houston, TX (US)

(73) Assignee: William Marsh Rice University, Houston, TX (US)

( * ) Notice: Subject to any disclaimer, the term of this patent is extended or adjusted under 35 U.S.C. 154(b) by 7 days.

(21) Appl. No.: 14/952,346

(22) Filed: Nov. 25, 2015

(65) Prior Publication Data

US 2016/0143538 A1 May 26, 2016

Related U.S. Application Data

(60) Provisional application No. 62/084,319, filed on Nov. 25, 2014.

(51) Int. Cl.
| | |
|---|---|
| A61B 5/00 | (2006.01) |
| A61B 5/024 | (2006.01) |
| A61B 5/11 | (2006.01) |
| G06K 9/00 | (2006.01) |
| G06K 9/20 | (2006.01) |
| G06K 9/46 | (2006.01) |

(52) U.S. Cl.
CPC ........ *A61B 5/0077* (2013.01); *A61B 5/02416* (2013.01); *A61B 5/02427* (2013.01); *A61B 5/1114* (2013.01); *A61B 5/7221* (2013.01); *A61B 5/7235* (2013.01); *A61B 5/7253* (2013.01); *G06K 9/00771* (2013.01); *G06K 9/2027* (2013.01); *G06K 9/4642* (2013.01); *G06K 9/4661* (2013.01)

(58) Field of Classification Search
None
See application file for complete search history.

(56) References Cited

U.S. PATENT DOCUMENTS

| | | | |
|---|---|---|---|
| 2014/0180132 | A1 | 6/2014 | Shan et al. |
| 2014/0275832 | A1 | 9/2014 | Muehlsteff et al. |

FOREIGN PATENT DOCUMENTS

| | | | |
|---|---|---|---|
| WO | 2014125250 A1 | 8/2014 | |

OTHER PUBLICATIONS

Lonneke A.M. Aarts et al.; "Non-contact heart rate monitoring utilizing camera photoplethysmography in the neonatal intensive care unit—A pilot study"; Early Human Development; vol. 89; pp. 943-948; 2013 (6 pages).

(Continued)

*Primary Examiner* — Brian T Gedeon
(74) *Attorney, Agent, or Firm* — Osha Liang LLP

(57) ABSTRACT

A system for estimating a photoplethysmogram waveform of a target includes an image processor configured to obtain images of the target and a waveform analyzer. The waveform analyzer is configured to determine a weight of a portion of the target. The weight is based on a time variation of a light reflectivity of the portion of the target. The time variation of the light reflectivity of the target is based on the images. The waveform analyzer is further configured to estimate a PPG waveform of the target based on the weight of the portion and the time variation of the light reflectivity of the portion.

18 Claims, 15 Drawing Sheets

(56) References Cited

OTHER PUBLICATIONS

John Allen; "Photoplethysmography and its application in clinical physiological measurement"; Physiol. Meas.; vol. 28; pp. R1-R39; 2007 (39 pages).
D. G. Brennan; "Linear Diversity Combining Techniques"; Proceedings of the IEEE; vol. 91; No. 2; pp. 331-356; Feb. 2003 (26 pages).
Martin A. Fischler et al.; "Random Sample Consensus: A Paradigm for Model Fitting with Applications to Image Analysis and Automated Cartography"; Communications of the ACM; vol. 24; No. 6; pp. 381-395; Jun. 1981 (15 pages).
James A.J. Heathers; "Smartphone-enabled pulse rate variability: An alternative methodology for the collection of heart rate variability in psychophysiological research"; International Journal of Psychophysiology; vol. 89; pp. 297-304; 2013 (8 pages).
Benjamin D. Holton et al.; "Signal recovery in imaging photoplethysmography"; Physiol. Meas.; vol. 34; pp. 1499-1511; 2013 (13 pages).
Sijung Hu et al.; "Opto-Physiological Modeling Applied to Photoplethysmographic Cardiovascular Assessment"; Journal of Healthcare Engineering; vol. 4; No. 4; pp. 505-528; 2013 (24 pages).
Kenneth Humphreys et al.; "Noncontact simultaneous dual wavelength photoplethysmography: A further step toward noncontact pulse oximetry"; Review of Scientific Instruments; vol. 78; pp. 044304-1 to 044304-6; 2007 (6 pages).
Zdenek Kalal et al.; "Forward-Backward Error: Automatic Detection of Tracking Failures"; International Conference on Pattern Recognition; Aug. 2010 (4 pages).
Magdalena Lewandowska et al.; "Measuring Pulse Rate with a Webcam—a Non-contact Method for Evaluating Cardiac Activity"; Proceedings of the Federated Conference on Computer Science and Information Systems; pp. 405-410; 2011 (6 pages).
Bruce D. Lucas et al.; "An Iterative Image Registration Technique with an Application to Stereo Vision"; Proc. 7th Intl. Joint Conf. on Artificial Intelligence (IJCAI); pp. 674-679; Aug. 1981 (6 pages).

Daniel McDuff et al.; "Improvements in Remote Cardiopulmonary Measurement Using a Five Band Digital Camera"; IEEE Transactions on Biomedical Engineering; vol. 61; No. 10; pp. 2593-2601; Oct. 2014 (9 pages).
M. Nitzan et al.; "The difference in pulse transit time to the toe and finger measured by photoplethysmography"; Physiol. Meas.; vol. 23; pp. 85-93; 2002 (9 pages).
Ming-Zher Poh et al.; "Non-contact, automated cardiac pulse measurements using video imaging and blind source separation."; Optics Express; vol. 18; No. 10; pp. 10762-10774; May 2010 (13 pages).
Ming-Zher Poh et al.; "Advancements in Noncontact, Multiparameter Physiological Measurements Using a Webcam"; IEEE Transactions on Biomedical Engineering; vol. 58; No. 1; pp. 7-11; Jan. 2011 (5 pages).
Jason M. Saragih et al.; "Deformable Model Fitting by Regularized Landmark Mean-Shift"; Int. J. Comput. Vis.; vol. 91; pp. 200-215; 2011 (16 pages).
Jianbo Shi et al.; "Good Features to Track"; IEEE Conference on Computer Vision and Pattern Recognition (CVPR94); 1994 (8 pages).
Yu Sun et al.; "Motion-compensated noncontact imaging photoplethysmography to monitor cardiorespiratory status during exercise"; Journal of Biomedical Optics; vol. 16; No. 7; pp. 077010-1 to 077010-9; Jul. 2011 (9 pages).
Carlo Tomasi et al.; "Shape and Motion from Image Streams: a Factorization Method—Part 3; Detection and Tracking of Point Features"; Technical Report CMU-CS-91-132; Apr. 1991 (22 pages).
Wim Verkruysse et al.; "Remote plethysmographic imaging using ambient light."; Optics Express; vol. 16; No. 26; pp. 21434-21445; Dec. 2008 (12 pages).
F. P. Wieringa et al.; "Contactless Mutliple Wavelength Photoplethysmographic Imaging: A First Step Toward 'SpO2 Camera' Technology"; Annals of Biomedical Engineering; vol. 33; No. 8; pp. 1034-1041; Aug. 2005 (8 pages).
International Search Report issued in corresponding Application No. PCT/US2015/062666, dated Feb. 26, 2016 (6 pages).
Written Opinion issued in corresponding Application No. PCT/US2015/062666, dated Feb. 26, 2016 (7 pages).

CAMERA BASED PHOTOPLETHYSMOGRAM ESTIMATION

STATEMENT REGARDING FEDERALLY SPONSORED RESEARCH OR DEVELOPMENT

The invention was made with government support under Grant Number CNS-1126478 awarded by the National Science Foundation. The invention was made with government support under Grant Number IIS-1116718 awarded by the National Science Foundation. The government has certain rights in the invention.

BACKGROUND

Measurements of a patient's vital signs may provide a physician or other individual with information related to the health and wellbeing of the patient. In some cases, vital signs are measured by placing a sensor in direct contact with a portion of the patient's body. For example, a chest strap or blood pressure cuff may be placed in direct contact with a patient to measure vital signs.

SUMMARY

In one aspect, a system for estimating a photoplethysmogram (PPG) waveform of a target in accordance with one or more embodiments of the invention includes an image processor configured to obtain images of the target; and a waveform analyzer configured to determine a weight of a portion of the target, based on a time variation light reflectivity of the portion of the target based on the images, and estimate a PPG waveform based on the weight of the portion and the time variation of the light reflectivity of the portion.

In one aspect, a method of estimating a PPG waveform of a target in accordance with one or more embodiments of the invention includes obtaining a plurality of images, wherein an image of the plurality of images comprises the target; subdividing the target into a plurality of portions; determining, based on the plurality of images, a time variation of a light reflectivity of a portion of the plurality of portions; determining, based on the time variation of the light reflectivity, a weight associated with the portion of the plurality of portions; and estimating the PPG waveform of the target based on the weight and the image of the plurality of images.

In one aspect, a non-transitory computer readable medium storing instructions for estimating a PPG waveform of a target in accordance with one or more embodiments of the invention includes instructions that include functionality for obtaining a plurality of images, wherein an image of the plurality of images comprises the target; subdividing the target into a plurality of portions; determining, based on the plurality of images, a time variation of a light reflectivity of a portion of the plurality of portions; determining, based on the time variation of the light reflectivity, a weight associated with the portion of the plurality of portions; and estimating the PPG waveform of the target based on the weight and the image of the plurality of images.

BRIEF DESCRIPTION OF DRAWINGS

Certain embodiments of the invention will be described with reference to the accompanying drawings. However, the accompanying drawings illustrate only certain aspects or implementations of the invention by way of example and are not meant to limit the scope of the claims.

DETAILED DESCRIPTION

Specific embodiments will now be described with reference to the accompanying figures. In the following description, numerous details are set forth as examples of the invention. It will be understood by those skilled in the art that one or more embodiments of the present invention may be practiced without these specific details and that numerous variations or modifications may be possible without departing from the scope of the invention. Certain details known to those of ordinary skill in the art are omitted to avoid obscuring the description.

Embodiments of the invention relate to systems and methods for measuring the vital signs of a target. The target may be a portion of a patient The vital signs may be measured by estimating a photoplethysmogram (PPG) waveform without direct contact with the target. The vital signs may be derived from the estimated PPG waveform.

A system in accordance with one or more embodiments of the invention may include one or more cameras that generate images of a target. The PPG waveform may be estimated based on the light reflectivity of one or more portions of the target. The light reflectivity of the one or more portions of the target may be determined based on the images of the target.

The system may include a waveform analyzer that determines a PPG waveform of a target based on images of the target. The images may be generated by the cameras. The waveform analyzer may subdivide a target into multiple portions and determine a quality of a PPG signal included in the light reflectivity of each portion of the multiple portions. The waveform analyzer may determine the quality of the PPG signal of each portion based on a time variation of the light reflectivity of each portion. The waveform analyzer may determine a total PPG waveform based on the light reflectivity of each portion and the quality of the PPG signal of each portion.

The system may include a target tracker that determines a location of a target within the image. The target tracker may generate a transformation based on the location of the target within the image that maps portions of the image to the target. For example, as a target moves, portions of the target may appear in different portions of multiple images of the target. The transformation may be used to map portions of each image to the target and thereby generate the time variation of light reflectivity of the target from the images. In one or more embodiments of the invention, the target may be a patient, e.g., a person, or a portion of the patient, e.g., the person's face.

Figure 1:
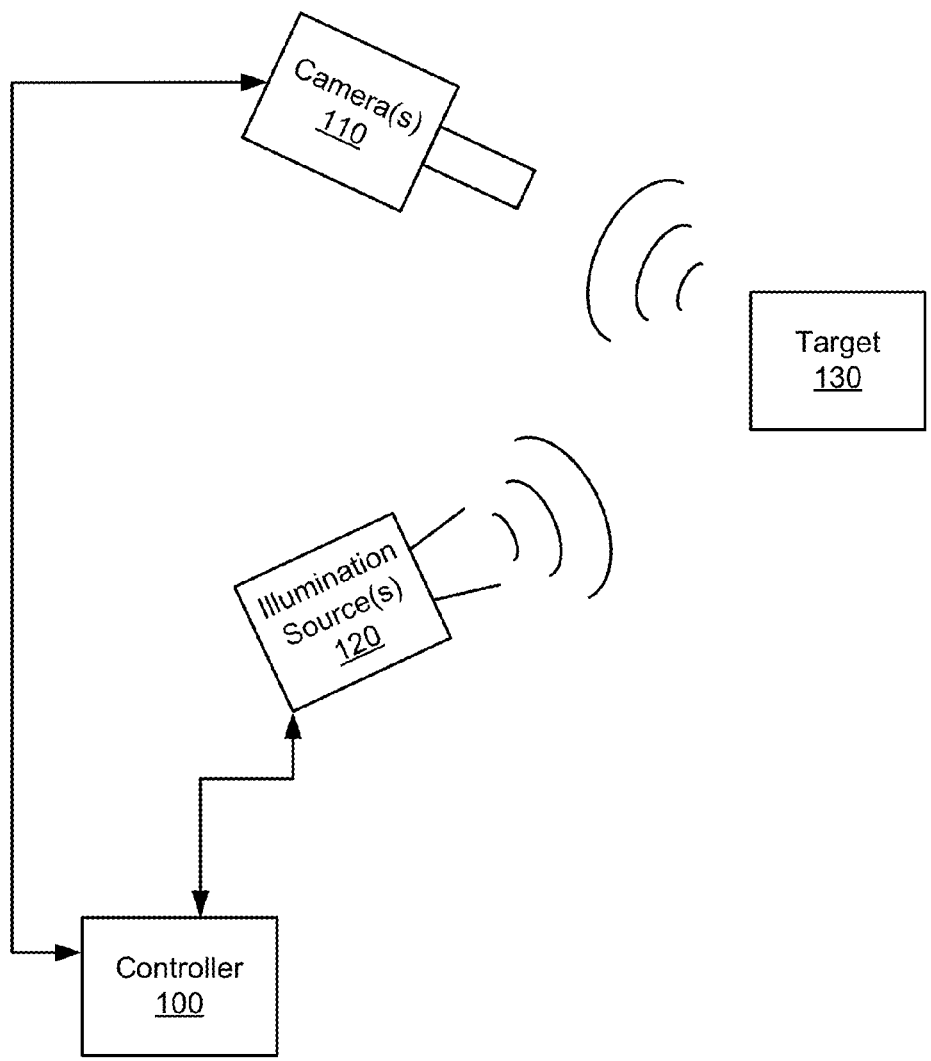
FIG. 1 shows a diagram of a system in accordance with one or more embodiments of the invention.

FIG. 1 shows a system in accordance with one or more embodiments of the invention. The system may determine vital signs of a target (130). The target may be, for example, a patient. The system may include one or more cameras (110), one or more illumination sources (120), and a controller (100). Each of the aforementioned components of the system are described below.

The system may include one or more cameras (110) configured to generate images of the target (130). The cameras (110) may be video or still image cameras. The cameras (110) may be operatively connected to the controller (100) and thereby may send images to the controller (100). The cameras (110) may be controllable by the controller (100) and may receive commands from the controller (100) by the operable connection. In one or more embodiments of the invention, the cameras (110) may be light-field cameras, infra-red cameras, hyper-spectral cameras, a monochrome image sensor, a panchromatic image sensor, a line sensor, or a combination of the aforementioned types of cameras. In one or more embodiments of the invention, each of the cameras (110) may produce a different view of the target (130), e.g., each camera may be located at different positions and/or angles relative to the target (130). In one or more embodiments of the invention, the cameras (110) may produce images without illumination provided by the illumination sources (120).

In one or more embodiments of the invention, each of the images generated by the cameras (110) may include pixels. Each of the pixels of each image may have a location that is relative to the frame of the image. Due to motion of the target, motion of the cameras, or other causes, the target may move with respect to the frame of each of the images that are captured at different times.

The system may include one or more illumination sources (120) configured to illuminate the target (130). The illumination sources (120) may be, for example, incandescent bulbs, fluorescent bulbs, or light emitting diodes. The illuminations sources (120) may generate an illumination that includes a broad spectral content, e.g., white light, or a narrow spectrum, e.g., blue light. In one or more embodiments of the invention, each of the illumination sources (120) may generate a different spectrum and thereby the target (130) may be illuminated with a configurable spectrum. The illumination source (120) may be operatively connected to the controller (100). The illumination sources may be controllable by the controller (100) and may receive commands from the controller (100) by the operable connection.

The system may include the controller (100). The controller (100) may be configured to determine vital signs of the target (130) based on images generated by the cameras (110). The controller (100) may also be configured to send commands to the cameras (110) and illumination sources (120) and thereby obtain images of the target (130).

Figure 2:
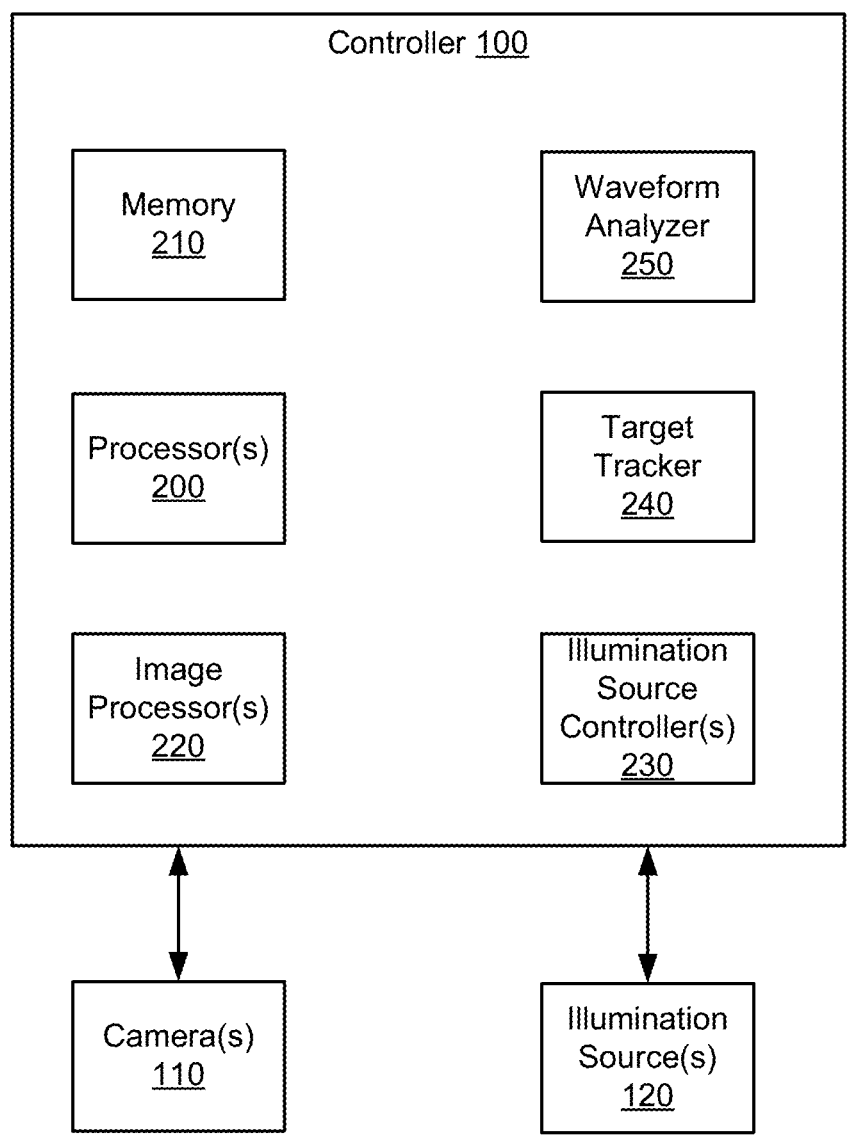
FIG. 2 shows a diagram of a controller in accordance with one or more embodiments of the invention.

FIG. 2 shows a controller (100) in accordance with one or more embodiments of the invention. The controller (100) may be a physical device that includes non-transitory storage, memory (e.g. Random Access Memory), and one or more processors. The non-transitory storage may include instructions which, when executed by the one or more processors, enable the system to perform the functions described in this application and shown in FIGS. 3-4.

The controller (100) may include one or more image processors (220), one or more illumination source controllers (230), a target tracker (240), and a waveform analyzer (250). Each of the components of the controller (100) is described below.

The image processors (220) may be configured to receive signals/data from the cameras (110) and extract images from the received signals/data. The image processors (220) may forward the extracted images to the memory, processors, target tracker, or waveform analyzer. In one or more embodiments of the invention, the image processors (220) may extract images from multiple cameras (110). The image processors (220) may be, for example, an embedded hardware device such as a field programmable gate array (FPGA), application specific integrated circuit (ASIC), and/or digital signal processor (DSP). Other embedded hardware devices may be used without departing from the invention.

In one or more embodiments of the invention, the image processors (220) may be configured to extract images from one or more video recordings and/or streaming videos comprising one or more frames including a target. For example, the image processors (220) may receive a video recording and extract images from frames of the video recording. In one or more embodiments of the invention, the image processors (220) may obtain multiple video recordings and/or streaming videos and extract images from one or more of the video recordings and/or streaming videos.

The illumination source controllers (230) may be configured to send and receive signals/data from the illumination sources (120). The illumination source controllers (230) may receive commands from the processor, waveform analyzer, or target tracker and operate the illumination sources (120) in accordance with the receive commands. For example, the illumination source controllers (230) may receive a command from a processor that indicates an illumination source (120) is to be activated. In response to receiving the command, the illumination source controllers (230) may activate the illumination source (120). The illumination source controllers (230) may be, for example, an embedded hardware device such as a field programmable gate array (FPGA), application specific integrated circuit (ASIC), and/or digital signal processor (DSP). Other embedded hardware devices may be used without departing from the invention.

The illumination source controllers (230) may be configured to send and receive signals/data from the illumination sources (120). The illumination source controllers (230) may receive commands from the processor, waveform analyzer, or target tracker and operate the illumination sources (120) in accordance with the receive commands. For example, the illumination source controllers (230) may receive a command from a processor that indicates an illumination source (120) is to be activated. In response to receiving the command, the illumination source controllers (230) may activate the illumination source (120). The illumination source controllers (230) may be, for example, an embedded hardware device such as a field programmable gate array (FPGA), application specific integrated circuit (ASIC), and/or digital signal processor (DSP). Other embedded hardware devices may be used without departing from the invention.

The waveform analyzer (250) may be executing on the controller (100). In one or more embodiments of the invention, the waveform analyzer (250) may be executing on another computational device without departing from the invention. For example, the waveform analyzer (250) may be executing on a cloud computing service linked to the controller by an operable connection.

The waveform analyzer (250) may be configured to estimate a PPG waveform based on images of a target. The waveform analyzer (250) may estimate the PPG waveform based on light reflectivity of a target. The waveform analyzer (250) may evaluate the spatial and temporal light reflectivity of the target to determine areas of the target that may include a stronger PPG waveform signal or a weaker PPG waveform signal. Based on the strength of the PPG waveform signal within the light reflectivity of the spatial area, the waveform analyzer (250) may generate a weight associated with the spatial area of the target. The waveform analyzer (250) may determine the total light reflectivity of the target based on the determined weight to estimate a PPG waveform of the target. The waveform analyzer (250) may implement the methods of identifying a target and generating alignment transformations as described with respect to FIGS. 4A-4B.

The target tracker (240) may be executing on the controller (100). In one or more embodiments of the invention, the target tracker (240) may be executing on another computational device without departing from the invention. For example, the target tracker (240) may be executing on a cloud computing service linked to the controller by an operable connection.

The target tracker (240) may be configured to identify a target within one or more images. The images may be obtained from the image processors (220). The target tracker (240) may generate alignment transformations for each image. Each alignment transformation may relates the portion of the image, e.g., a number of pixels, to a portion of a target, e.g., a spatial area of the target. The alignment transformations may be used to correlate portions of each image associated with a portion of the target and thereby determine the light reflectivity of a portion of the target based on the images. The target tracker (240) may implement the methods of identifying a target and generating alignment transformations as described with respect to FIGS. 4A-4B.

Figure 3A:
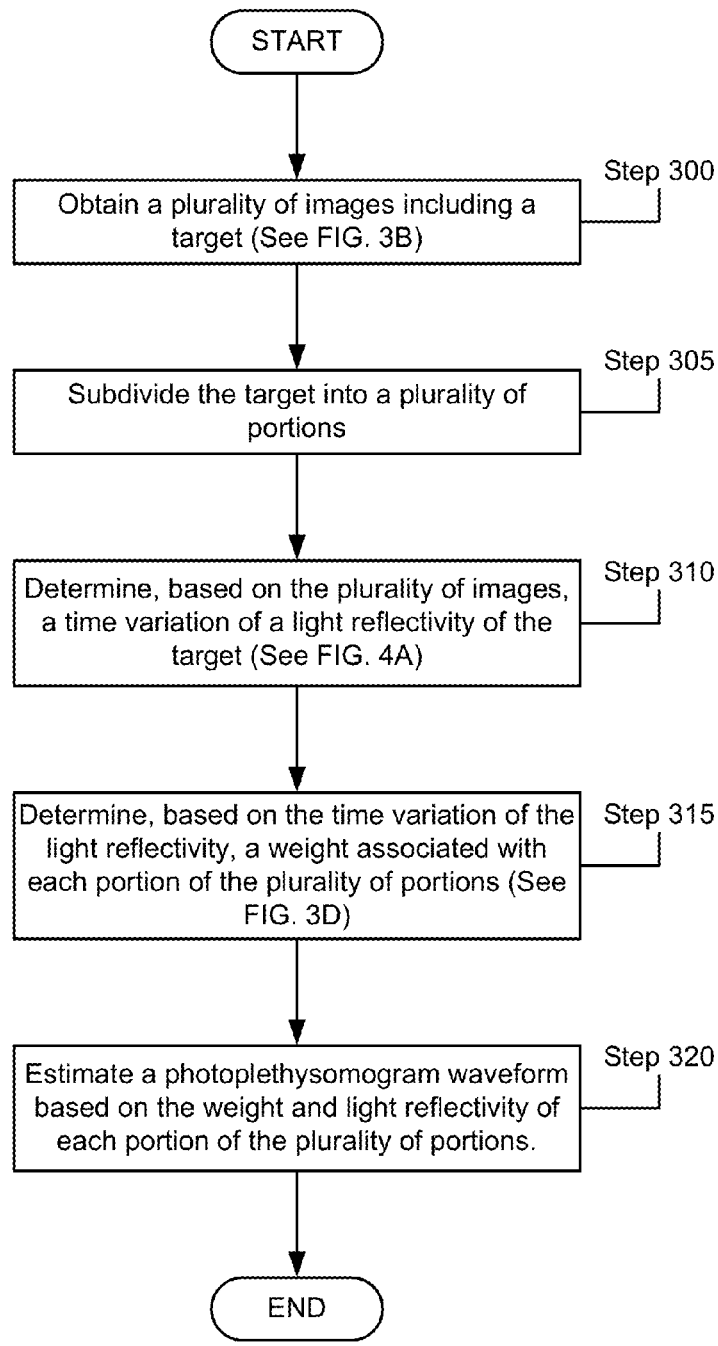
FIG. 3A shows a flowchart of a method of estimating a photoplethysmogram (PPG) waveform in accordance with embodiments of the invention.

FIG. 3A shows a flowchart of a method in accordance with one or more embodiments of the invention. The method depicted in FIG. 3A may be used to estimate a PPG waveform of a target in accordance with one or more embodiments of the invention. One or more steps shown in FIG. 3A may be omitted, repeated, and/or performed in a different order among different embodiments.

In Step 300, a waveform analyzer obtains a plurality of images including a target. The target may be, for example, a portion of a patient such as the face of the patient. Each of the images may be at different times and thereby include the light reflectivity of the target over time, e.g., the temporal variation of the light reflectivity of the target. The waveform analyzer may obtain the images from one or more cameras. The images may be obtained by the method shown in FIG. 3B.

In Step 305, the waveform analyzer subdivides the target into a plurality of portions. Each portion may be a spatial area of the target.

In one or more embodiments of the invention, the spatial area of each portion of the target may be equal in size. For example, the target may be uniformly divided into portions of equal area.

In one or more embodiments of the invention, the spatial area of each portion of the target may be different in size. For example, some portions may include a larger spatial area of the target than other portions of the target.

In Step 310, the waveform analyzer determines, based on the obtained plurality of images, a light reflectivity of each portion of the target. The light reflectivity of the target may be determined based on the pixels that are associated with the target in each of the images. For example, each pixel of an image may indicate a magnitude and/or a frequency/spectrum of the light reflectivity of a portion of the target at a specific time. Multiple pixels of an image may be associated with a portion of the target. The light reflectivity of each portion of the target may be determined by averaging the pixels associated with the portion of the target. The time variation of the light reflectivity of the target may be determined based on the difference between the light reflectivity of the target in each image. The pixels associated with each portion of the target may be determined by the method shown in FIG. 4A.

In Step 315, the waveform analyzer determines a weight associated with each portion of the plurality of portions based on the time variation of the light reflectivity of each portion of the target. The weight associated with each portion of the target may indicate a relative strength of a PPG waveform signal included in the light reflectivity of each portion of the target. In other words, the light reflectivity of some portions of the target may be strongly correlated with a total PPG waveform and other portions of the target may be weakly correlated with the total PPG waveform. The weight of each portion of the target may be determined by the method shown in FIG. 3D.

In Step 320, the waveform analyzer estimates a PPG waveform of the target based on the weight of each portion of the target and the temporal variation of the light reflectivity of each portion. The PPG waveform may be estimated by bandpass filtering the time variation of the light reflectivity of each portion to remove low frequency components, such as the constant reflectivity of the skin, and high frequency components away from a potential PPG signal. In one or more embodiments of the invention, the bandpass filter has a bandwidth of 0.5 Hz to 5 Hz. The filtered light reflectivity of each portion of the target may be represented as:

$$\hat{y}_n(t) \qquad \text{(Equation 1)}$$

where n is a portion of the target.

A summation of the filtered light reflectivity of each portion of the target multiplied by the weight of the portion may be formed to estimate the total PPG waveform of the target. The estimated PPG waveform of the target may be represented as:

$$p_{est}(t) = \Sum_{i=1}^{N} G_i \hat{y}_i(t) \quad \text{(Equation 2)}$$

where $G_i$ is the weight of a portion of the target and N is the total number of portions of the target.

In one or more embodiments of the invention, a reject filter may be used when forming the summation to determine the PPG waveform. In general, the strength of the PPG waveform within the light reflectivity of each portion of the target is expected to be small. A reject filter may be used to remove the contribution of any portion of the target that has a large light reflectivity value. When using a reject filter, the estimated PPG waveform of the target may be represented as:

$$p_{est}(t) = \Sum_{i=1}^{N} G_i \hat{y}_i(t) I(\text{amp}(\hat{y}_n(t)) < \tau_{amp}) \quad \text{(Equation 3)}$$

Where I is an indicator function, amp( ) is the maximum amplitude of the signal over a T seconds duration, and $\tau_{amp}$ is a threshold value.

Thus the method shown in FIG. 3A may be used to estimate a total PPG waveform of a target. The estimated PPG waveform may be subsequently used to determine one or more vital signs of the target.

Figure 3B:
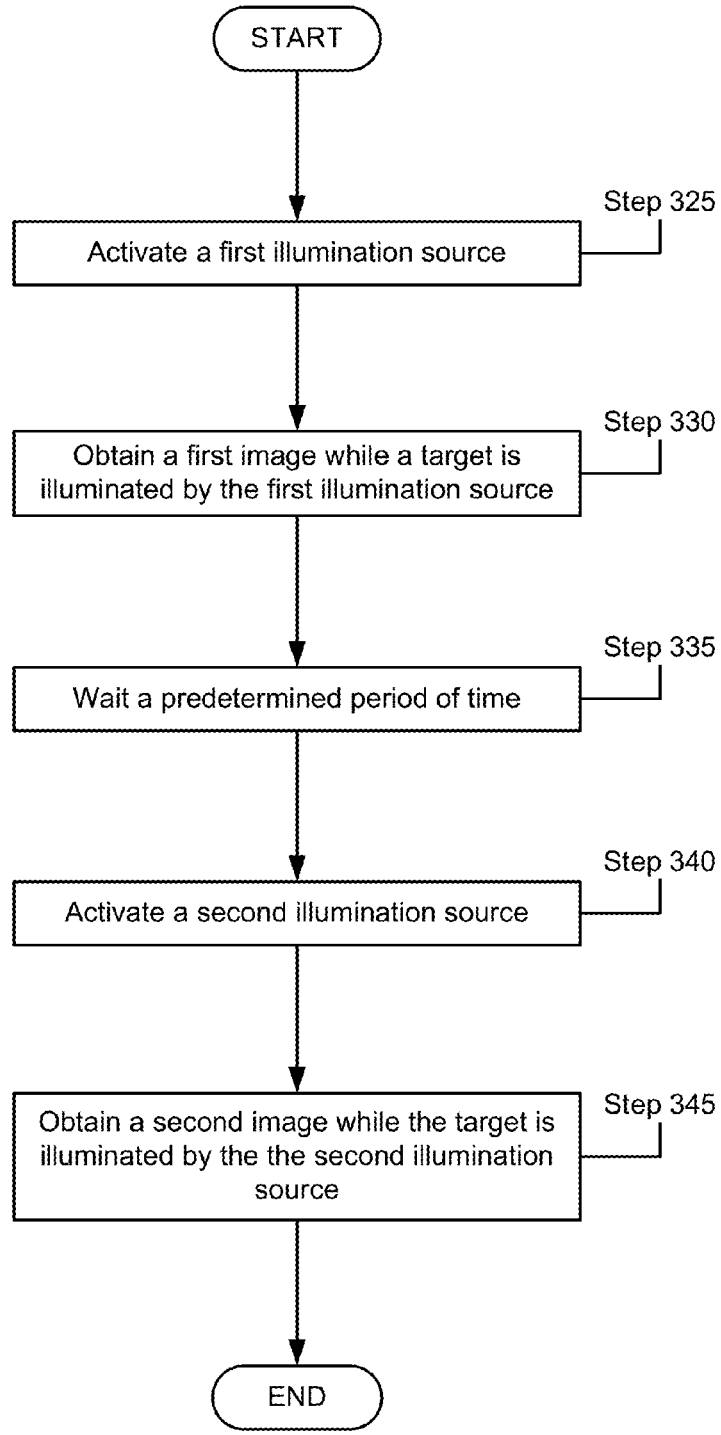
FIG. 3B shows a flowchart of a method of generating images of a target in accordance with embodiments of the invention.

FIG. 3B shows a flowchart of a method in accordance with one or more embodiments of the invention. The method depicted in FIG. 3B may be used to obtain one or more images of a target in accordance with one or more embodiments of the invention. One or more steps shown in FIG. 3B may be omitted, repeated, and/or performed in a different order among different embodiments.

In Step 325, a first illumination source is activated. The first illumination source may be, for example, an incandescent bulk, fluorescent bulb, light emitting diode, or any other light source. In one or more embodiments of the invention, the first illumination source may have a first spectral content that covers only a portion of the visible spectrum.

In Step 330, a first image of a target is obtained while the a target is illuminated by the first illumination source. The first image may be obtained by a camera.

In Step 335, a first image of a target is obtained while the target is illuminated by the first illumination source. The first image may be obtained by a first camera.

In Step 340, a second illumination source is activated. The second illumination source may be, for example, an incandescent bulk, fluorescent bulb, light emitting diode, or any other light source. In one or more embodiments of the invention, the second illumination source may have a second spectral content that is different than the first spectral content of the first illumination source.

In Step 345, a second image of the target is obtained while the target is illuminated by the second illumination source. The second image may be obtained by the first camera or another camera. In one or more embodiments of the invention, the second image may be taken at a second time that is different than a first time at which the first image is taken.

In one or more embodiments of the invention, the second image may be taken at a time that is the same as the time at which the first image is taken. The second image may be taken from a different angle or location, with respect to the target, so that the second image of the target images portions of the target that were occluded in the first image.

In one or more embodiments of the invention, Steps 325-345 may be repeated to generate multiple images of the target at different points in time to image the light reflectivity of the target over a period of time.

Thus the method shown in FIG. 3B may be used to obtain one or more images of a target, from one or more angles, and at one or more points in time.

Figure 3C:
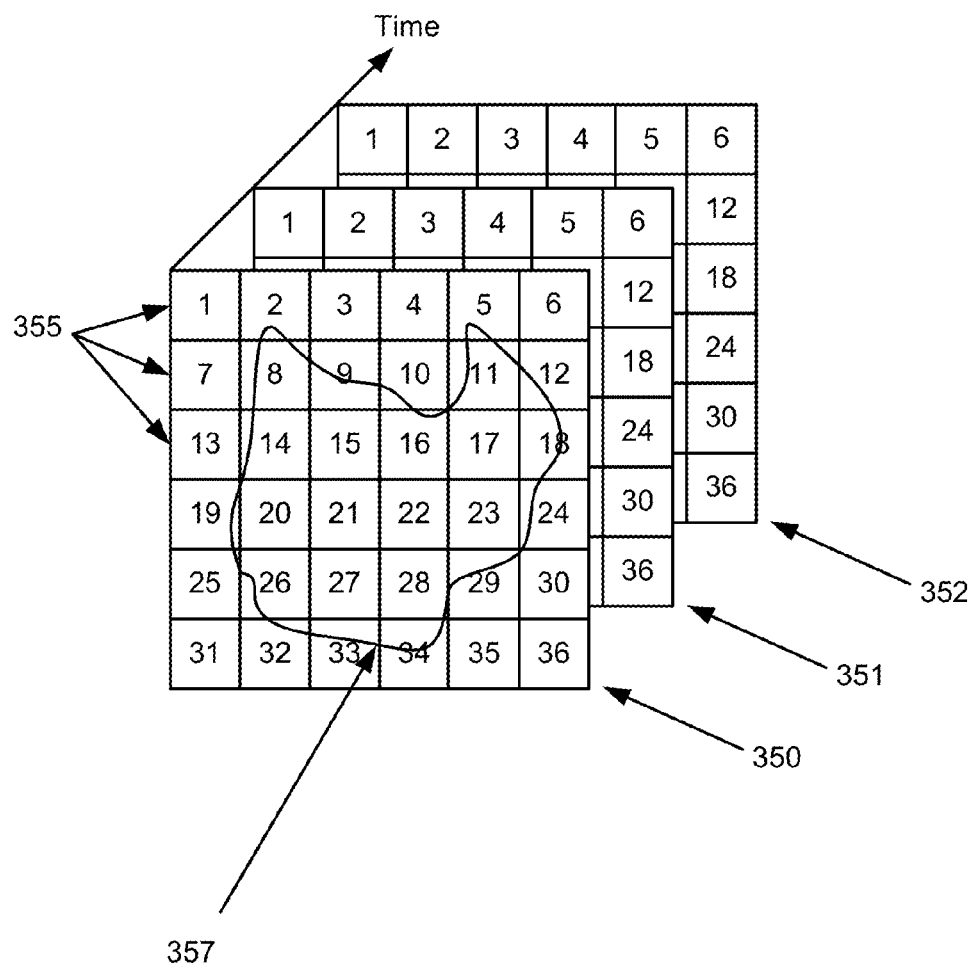
FIG. 3C shows a diagram of multiple images of a target in accordance with embodiments of the invention.

FIG. 3C shows an example diagram illustrating three images (350, 351, 352) of a target taken at three different points in time in accordance with one or more embodiments of the invention. The first image (350) includes pixels (355) obtained by a camera. Specifically, the first image (350) includes 36 pixels (each pixel is numbered). The first image (350) could include any number of pixels without departing from the invention. A target (357) is superimposed over the first image (350) to indicate that not all of the pixels of the first image (350) correspond to the target (357) and that some pixels of the first image (350) may correspond to different portions of the target (357). In other words, some of the pixels of the first image do not show the target (357) and the pixels that do show the target may correspond to a specific portion of the target. For example, some of the pixels could show a portion of a background next to a target (357) and thereby not be associated with any portion of the target (357). In another example, pixel 11 of the first image (350) may only correspond to the top right portion of the target (357).

The second image (351) includes 36 pixels like the first image (350) but the second image (351) was taken at a different point in time than the first image (350). Similar or different pixels of the second image (351), when compared to the pixels of the first image that correspond to the target, may correspond to the target (357). The second image (351) could include any number of pixels without departing from the invention.

The third image (352) also includes 36 pixels like the first image (350) and second image (351) was taken at a different point in time than either of the first image and second image. The third image (352) could include any number of pixels without departing from the invention.

Each of the three images may include pixels that correlate with portions of the target at different points of time and thereby may be used to determine the light reflectivity of each portion of the target over time. However, due to movement of the target or other causes, the pixels of each of the three images associated with a particular portion of the target may be different in each of the three images. As will be described with respect to FIG. 4A, each image of the three images may be analyzed to determine which pixels of each image correspond with each portion of the target.

Figure 3D:
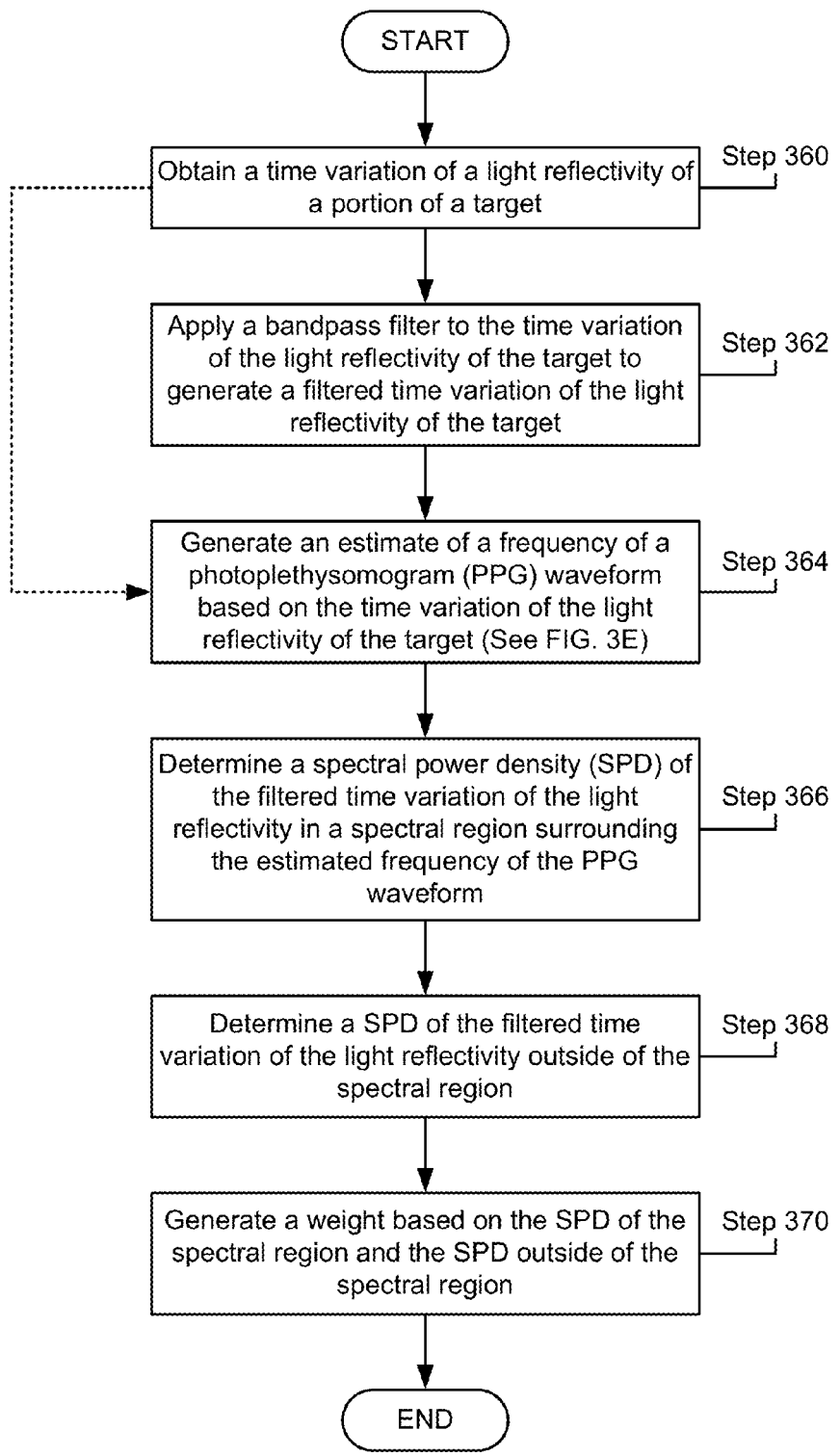
FIG. 3D shows a flowchart of a method of generating weights of portions of the target in accordance with embodiments of the invention.

FIG. 3D shows a flowchart of a method in accordance with one or more embodiments of the invention. The method depicted in FIG. 3D may be used to determine a weight of the light reflectivity of a portion of a target in accordance with one or more embodiments of the invention. One or more steps shown in FIG. 3D may be omitted, repeated, and/or performed in a different order among different embodiments.

In Step 360, a time variation of a light reflectivity of a portion of a target is obtained. The time variation of the light reflectivity of the portion of the target may be obtained based on pixels, associated with the portion of the target, from images of the target taken at different points in time. The images may be obtained by the method shown in FIG. 3B.

In Step 362, a bandpass filter is applied to the time variation of the light reflectivity of the portion of the target to generated a filtered time variation of the light reflectivity of the portion of the target. Bandpass filtering the time variation of the light reflectivity of the portion of the target target may remove low and high frequency light reflectivity information that is not associated with a PPG waveform. The bandpass filter may have a passband of 0.5 to 5 Hz.

In Step 364, an estimate of a frequency of PPG waveform is generated. The coarse estimate may be generated by the method shown in FIG. 3E.

In Step 366, a spectral power density of the time variation of the filtered light reflectivity in a spectral region surrounding the estimated frequency of the PPG waveform is determined. The spectral power density may be determined by transforming the time variation of the light reflectivity to a spectral representation of the light reflectivity and integrating the spectral power in the spectral region near the frequency of the PPG waveform generated in Step 364.

In Step 368, the spectral power density of the filtered light reflectivity outside of the spectral region surrounding the estimated frequency of the PPG waveform is determined. The spectral power density may be determined by transforming the filtered time variation of the filtered light reflectivity to a spectral representation of the light reflectivity and integrating the spectral power outside of the spectral region near the frequency of the PPG waveform generated in Step 364. In one or more embodiments of the invention, the spectral representation of the light reflectivity of the portion of the target may be formed by taking the Fourier transform of the time variation of the light reflectivity of the portion of the target.

In Step 370, a weight of the portion of the target is generated. The weight of the portion of the target may be generated by forming a ratio of the spectral power determined in Step 366 to the spectral power determined in Step 368. In other words, the ratio be may be the spectral power near the estimated frequency of the PPG waveform divided by the spectral power away from the estimated frequency of the PPG. Ratios of a higher value may indicate a stronger association between the light reflectivity of the portion and the PPG waveform. The weight of the portion of the target may be represented as:

$$G_i = \frac{\int_{PR-b}^{PR+b} \hat{Y}_i(f) df}{\int_{Min}^{Max} \hat{Y}_i(f) df - \int_{PR-b}^{PR+b} \hat{Y}_i(f) df}$$

(Equation 4)

where PR is the coarse estimate of the frequency of the PPG waveform, b is a small value that defines a spectral region around the frequency of the PPG waveform, Min is the minimum frequency of the spectral power density of the time variation of the light reflectivity of the portion, Max is the maximum frequency of the spectral power density of the time variation of the light reflectivity of the portion, and $\hat{Y}_i(f)$ is the spectral power density of the filtered time variation of the reflectivity of the portion of the target.

Thus, the method shown in FIG. 3D may be used to determine the weight of each portion of the target by repeating the method shown in FIG. 3D for each portion of the target.

Figure 3E:
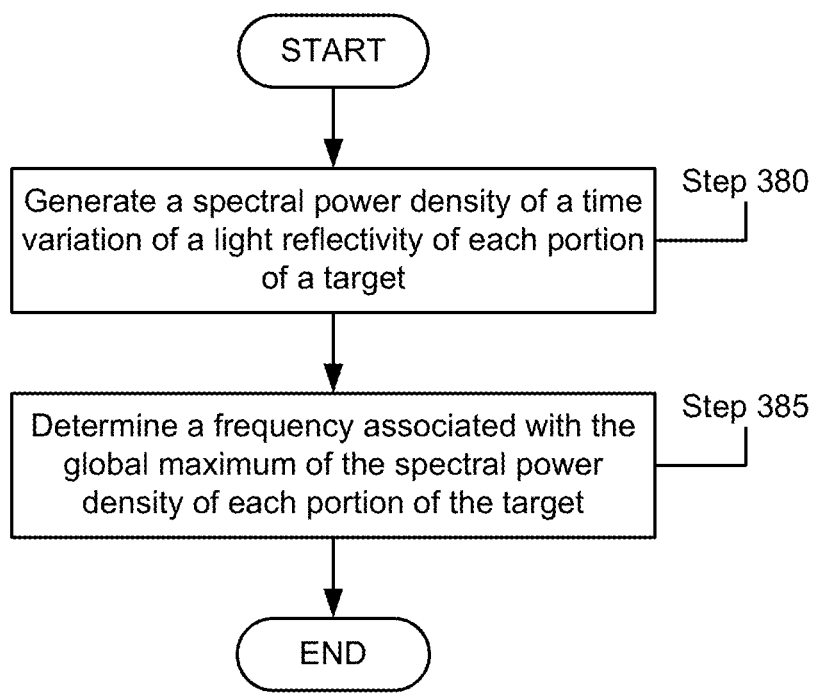
FIG. 3E shows a flowchart of a method of generating a coarse estimate of a frequency of a PPG waveform in accordance with embodiments of the invention.

FIG. 3E shows a flowchart of a method in accordance with one or more embodiments of the invention. The method depicted in FIG. 3E may be used to determine a coarse estimate of a frequency of a PPG waveform in accordance with one or more embodiments of the invention. One or more steps shown in FIG. 3E may be omitted, repeated, and/or performed in a different order among different embodiments.

In Step 380, a spectral power density of the time variation of light reflectivity of each portion of a target may be determined. The spectral power density of each portion may be determined by transforming the time variation of the light reflectivity of each portion to a spectral representation of the light reflectivity. In one or more embodiments of the invention, the spectral representation of the light reflectivity of each portion of the target may be formed by taking the Fourier transform of the time variation of the light reflectivity of each portion of the target.

In Step 390, a frequency associated with the global maximum of the spectral power density of each portion is determined. The global maximum of each spectral power density may be determined using any suitable global maximum finding method such as, for example, comparing the magnitude of each frequency to the magnitude of each other frequency. The coarse estimate of the frequency of the PPG waveform may be determined by averaging the determined frequencies of the global maximums.

Thus, the method shown in FIG. 3E may be used to determine a coarse estimate of the frequency of the PPG waveform. Additionally, the coarse estimate of the frequency of the PPG waveform may be used to determine the heart rate of the target and/or variability of the heart rate of the target, directly, without determining the PPG waveform of the target. The estimated frequency of the PPG waveform may be the heart rate of the target and the heart rate variability of the target may be determined by performing the method shown in FIG. 3E at different times and determining the variability of the heart rate of the target over time.

The methods shown in FIGS. 3A-3E may be used to estimate the PPG waveform of a target based on the light reflectivity of the target. As discussed with respect to FIGS. 3A and 3B, the light reflectivity of the target may be determined based on one or more images of the target.

Figure 4A:
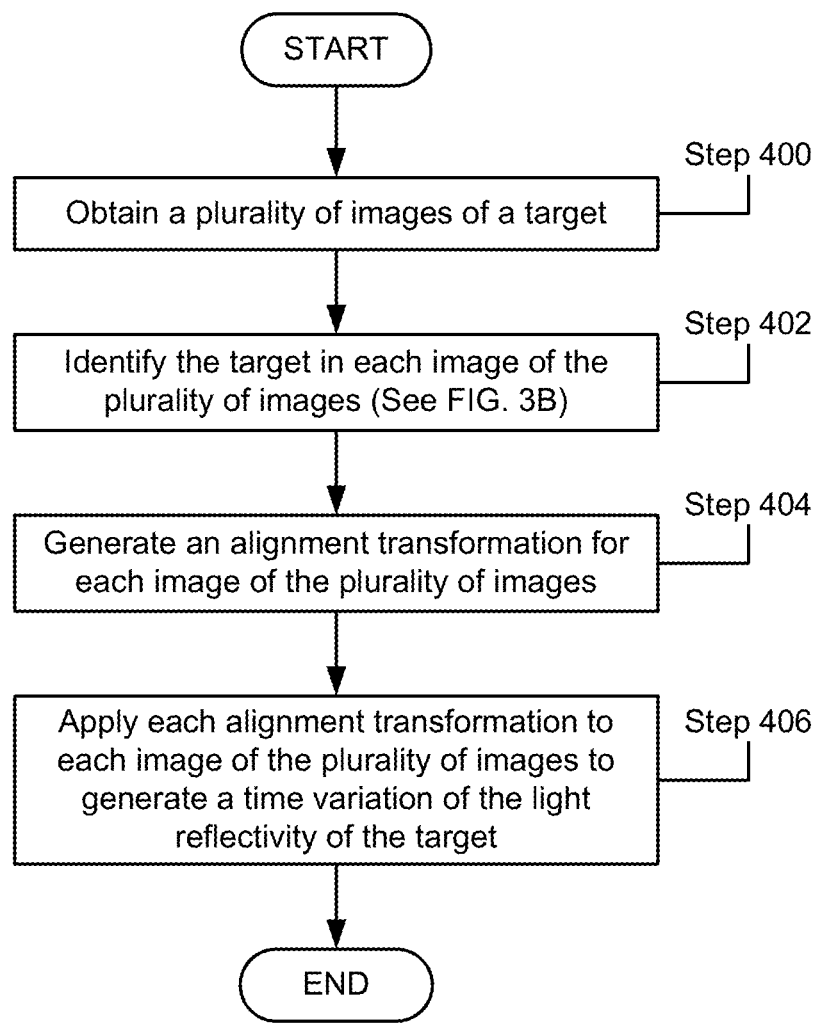
FIG. 4A shows a flowchart of a method of determining a relationship between pixels of one or more images and the light reflectivity of a target in accordance with embodiments of the invention.

FIG. 4A shows a flowchart of a method in accordance with one or more embodiments of the invention. The method depicted in FIG. 4A may be used to determine a relationship between pixels of one or more images and the light reflectivity of a target included in the images in accordance with one or more embodiments of the invention. One or more steps shown in FIG. 4A may be omitted, repeated, and/or performed in a different order among different embodiments.

In Step 400, images of a target are obtained. The images may be obtained by the method shown in FIG. 3B.

In Step 402, the target is identified in each of the images. The target in each of the images may be identified by the method shown in FIG. 4B.

In Step 404, alignment transformations for each image of the plurality of images are generated. The alignment transformation for each image may be generated based on a difference in the location of the target identified in each of the obtained images. For example, the pixels of each figure that are associated with any portion of the target may be different in each of the images. The alignment transformation of an image of the images may be the difference between the location of the target in a first image and the location of the target in a second image.

In one or more embodiments of the invention, the alignment transformation may be a spatially varying transformation. For example, in a first image the target may be a face of a patient. In a second image, the patient may yawn which distorts the shape and spatial structure of the target. The alignment transformation may associate pixels of the second image with portions that vary spatially due to the distorted shape of the target in the second image. In one or more embodiments of the invention, the alignment transformation may be a rigid affine fit.

In Step 406, each alignment transform may be applied to an associated image. Applying the alignment transform may form associations between each pixel of each image with a portion of the target and thereby enable the time variation of the light reflectivity of the target to be determined from the images.

A time variation of the light reflectivity of the target may be generated based on the time each image of the plurality of images was taken and the associations between the pixels of each image and the target. In other words, the light reflectivity of the target at the time an image was taken may be determined based on the associations between pixels of the image and the target. The time variation of the light reflectivity of the target may be determined based on the differences between the light reflectivity of the target in each image and corresponding to the time each images was taken.

In one or more embodiments of the invention, applying the alignment transformation to an image may rearrange the pixels in the image. Rearranging the pixels in the image may conform pixels of the image with a portion of the target. By rearranging the pixels of each image, the same pixels of each image may be associated with the same portions of the target.

In one or more embodiments of the invention, applying the alignment transformation to an image may add metadata to each pixel of the image that associates each pixel of the image with a portion of the target. By adding metadata to each pixel, the pixels associated with any portion of the target may be rapidly identified.

In one or more embodiments of the invention, portions of the target that are known to not be strongly associated with a PPG waveform are excluded during the alignment transforms. For example, the light reflectivity of the eyes of a patient may not be associated with a PPG waveform. Pixels of an image associated with the eyes of the patient may be ignored and/or excluded during the process of generating an alignment transformation and thereby remove areas of an image that would only contribute noise to the estimate of the total PPG waveform of the target.

Thus, the method shown in FIG. 4A may enable pixels of images to be associated with a target within the image and thereby remove or reduce the impact of movement and/or distortion of the target in each of the images.

Figure 4B:
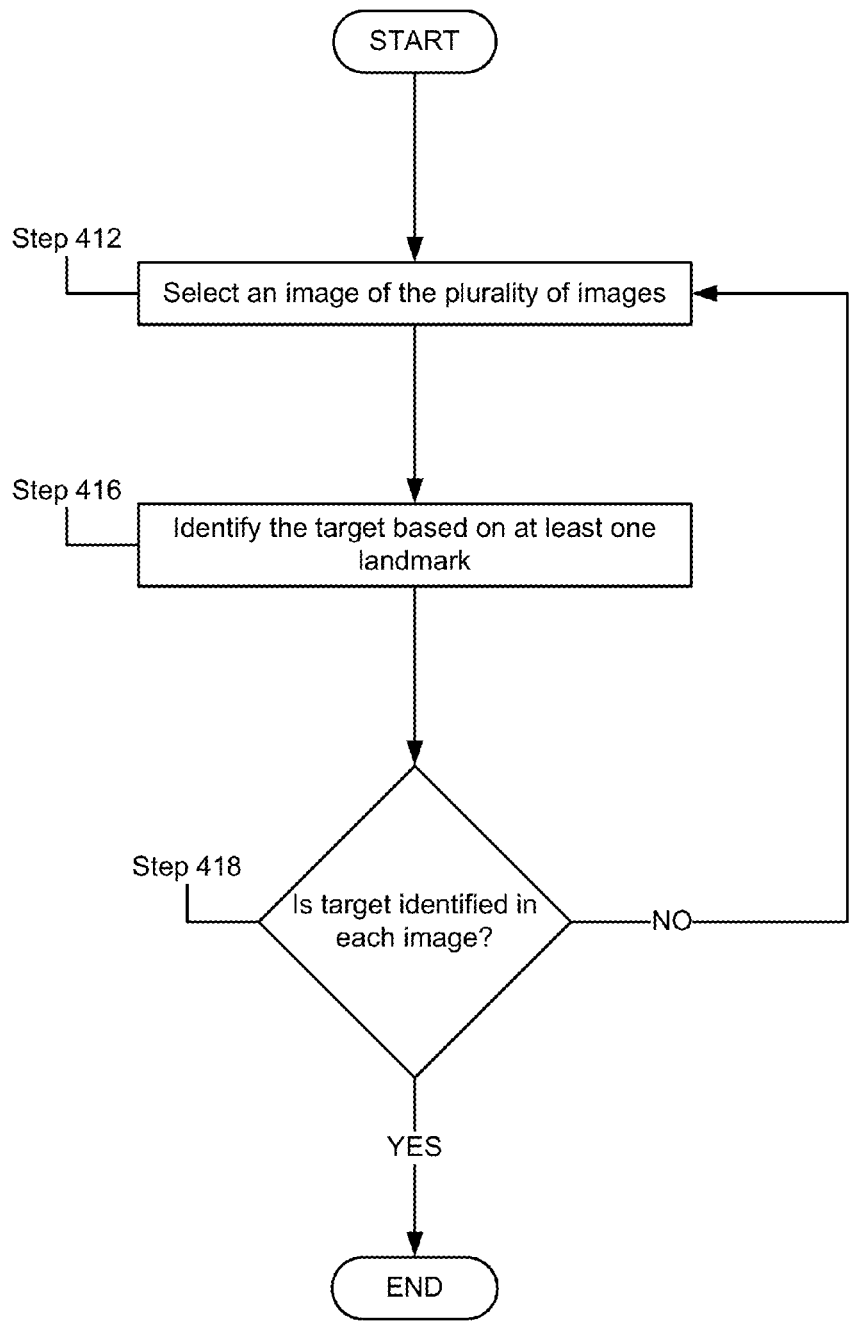
FIG. 4B shows a flowchart of a method of identifying a target in images in accordance with embodiments of the invention.

FIG. 4B shows a flowchart of a method in accordance with one or more embodiments of the invention. The method depicted in FIG. 4B may be used to identify a target in images in accordance with one or more embodiments of the invention. One or more steps shown in FIG. 4B may be omitted, repeated, and/or performed in a different order among different embodiments.

In Step 412, one of the images is selected.

In Step 416, the target is identified in the selected image based on at least one landmark. The target may be identified by comparing the spacing of the at least one landmark to the reference image.

In Step 418, it is determined whether a target has been identified in each of the images. If the target has not been identified in each of the images, the method may proceed to Step 412. If the target has been identified in each of the images, the method may end.

Thus, the method shown in FIG. 4B may be used to identify a target in any number of images.

The following examples are for explanatory purposes and are not intended to limit the scope of the technology.

Example 1

Figure 5A:
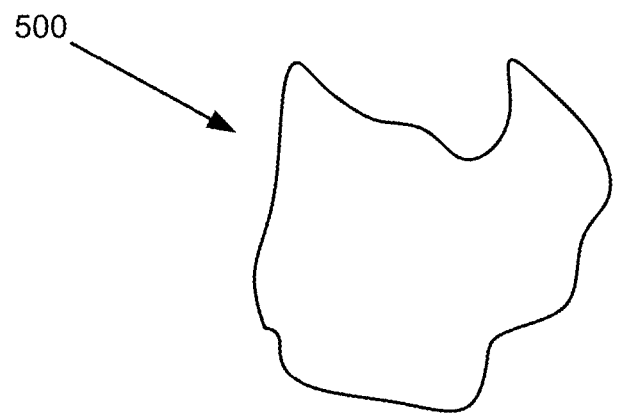
FIG. 5A shows an example of a target in accordance with embodiments of the invention.

FIG. 5A shows an example of a target (500). The target may be a portion of a patient. It may be desired to estimate a PPG waveform of the target to determine the vital signs of the target. The PPG waveform of the target may be estimated by the methods shown in, e.g., FIGS. 3A-4B.

To estimate the PPG waveform, a number of images including the target (500) may be taken at different points in time. For example, the images may be taken every 0.25 seconds for 20 seconds.

The target (500) in each of the images may be identified based on one or more landmarks of the target. For example, the target in each of the images may be identified based on a location of the eyes, nose, and facial outline of the target.

Based on the identified target in each image, an alignment transformation between the target in each image and the pixels of each image may be generated. For example, each of the images may include small movements of the target that change the location of the target and/or distort the target. The alignment transformation may add metadata to each pixels of the target to associate the pixel with a spatial location of the target.

Figure 5B:
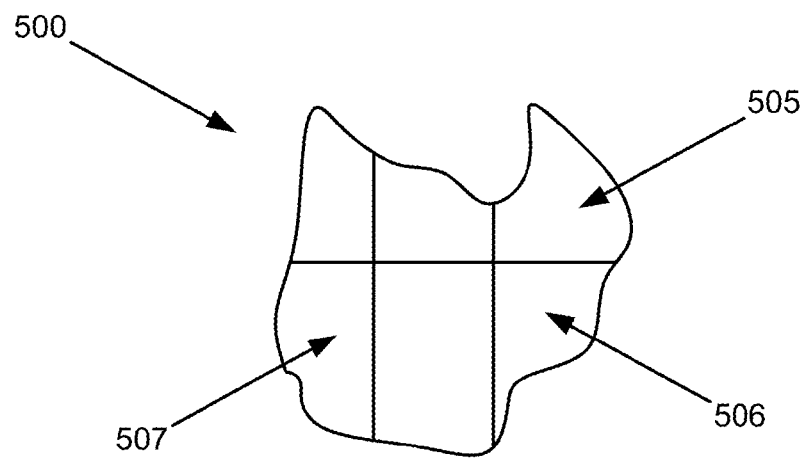
FIG. 5B shows an example of a subdivided target in accordance with embodiments of the invention.

The target may be subdivided into a number of portions. FIG. 5B shows an example of the target (500) divided into portions. Specifically, the target is divided into six portions including a first portion (505), second portion (506), and third portion (507).

The time variation of the light reflectivity of each of the first portion (505), second portion (506), and third portion (507) may be determined based on the pixels that include metadata that associates the pixels with each portion.

Figure 5C:
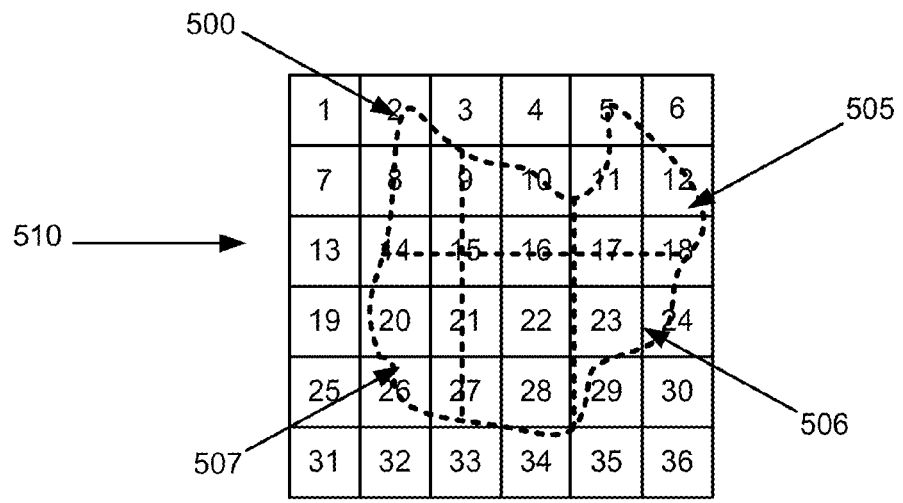
FIG. 5C shows an example of a target superimposed over a first image in accordance with embodiments of the invention.

FIG. 5C shows an example of a target (500) superimposed over a first image (510). The first image includes 36 pixels that are accordingly numbered. The superimposed target (500) indicates the association between pixels of the first image (510) each of the first portion (505), second portion (506), and third portion (507) of the target. For example, pixels 5, 11, 12, 17, and 18 are associated with the first portion (505), pixels 17, 18, 23, 24, and 29 are associated with the second portion (506), and pixels 14, 15, 20, 21, 26, and 27 are associated with the third portion (507). Thus, the light reflectivity of the first portion (505) of the target (500) at the time when the first image (510) was taken may be determined based on the values of pixels 5, 11, 12, 17, and 18.

Figure 5D:
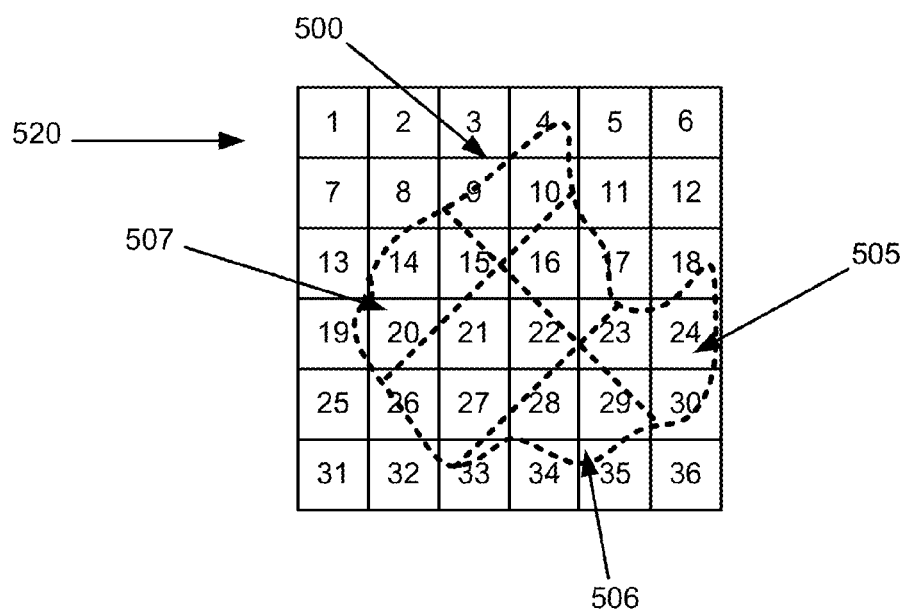
FIG. 5D shows an example of a target superimposed over a second image in accordance with embodiments of the invention.

FIG. 5D shows an example of a target (500) superimposed over a second image (520) that was taken at a different time than the first image. As seen from the second image (520), the target (500) is rotated with respect to the first image (510) and thereby different pixels are associated with each of the first portion (505), second portion (506), and third portion (507) of the target (500). For example, pixels 18, 23, 24, 29, and 30 are associated with the first portion (505), pixels 22, 23, 28, and 29 are associated with the second portion (506), and pixels 8, 9, 14, 15, 19, 20, and 21 are associated with the third portion (507). Thus, the light reflectivity of the first portion (505) of the target (500) at the time when the second image (520) was taken may be determined based on the values of pixels 18, 23, 24, 29, and 30.

Figure 5E:
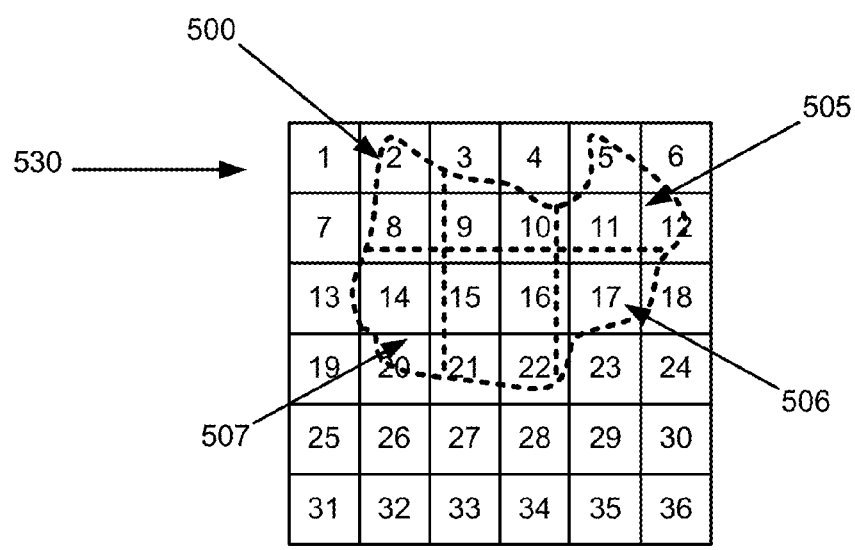
FIG. 5E shows an example of a target superimposed over a third image in accordance with embodiments of the invention.

FIG. 5E shows an example of a target (500) superimposed over a third image (530) that was taken at a different time than the first image and second image. As seen from the third image (530), the target (500) is distorted with respect to the first image (510) and thereby different pixels are associated with each of the first portion (505), second portion (506), and third portion (507) of the target (500). For example, pixels 5, 6, 10, 11, and 12 are associated with the first portion (505), pixels 10, 11, 12, 16, 17, 18, and 22 are associated with the second portion (506), and pixels 8, 9, 13, 14, 15, 20, and 21 are associated with the third portion (507). Thus, the light reflectivity of the first portion (505) of the target (500) at the time when the third image (530) was taken may be determined based on the values of pixels 5, 6, 10, 11, and 12.

Returning to FIG. 5B, weights of each of the first portion (505), second portion (506), and third portion (507) of the target (500) may be determined based on the time variation of the light reflectivity of each portion. With respect to the examples shown in FIGS. 5C-5E, the time variation of the light reflectivity of the first portion (505) may be determined by averaging the pixels associated with the first portion (505) of the first image (510) to determine a light reflectivity of the first portion (505) at the time when the first image was taken. The light reflectivity at the time of the second image (520) may be determined similarly by averaging the pixels of the second image (520) associated with the first portion (505). The light reflectivity at the time of the third image (530) may be determined similarly by averaging the pixels of the third image (530) associated with the first portion (505).

The time variation of the light reflectivity of each portion of the target may be determined by separately averaging the pixels of each image associated with each portion of the target and associating the averaged value of each image with a capture time of each image. For example, with respect to the first portion (505), pixels 5, 11, 12, 17, and 18 of the first image may be averaged and associated with the capture time of the first image, pixels 18, 23, 24, 29, and 30 of the second image may be averaged and associate with the capture time of the second image, and pixels 5, 6, 10, 11, and 12 of the third image may be averaged and associated with the capture time of the third image to determine the time variation of the light reflectivity of the first portion. The processes may be repeated for each portion to determine the time variation of the light reflectivity of each portion of the target.

The weights of each portion of the target (500) may be determined as described with respect to, e.g., FIGS. 3D and 3E by filtering the time variation of the light reflectivity of each portion, generating a coarse estimate of a frequency of a PPG waveform, and then forming a ratio of the spectral contention of the time variation of the light reflectivity near the frequency of the PPG waveform and away from the PPG waveform.

For example, the spectral power density of the time variation of the light reflectivity of the first portion may be determined by taking the Fourier transform of the time variation. The spectral power associated with the PPG waveform may be determined by integrating the spectral power density in a region near the PPG waveform and the spectral power that is not associated with the spectral power of the PPG waveform may be determined by integrating the spectral power density outside of the spectral region near the PPG waveform. The weight may then be determined by taking a ratio of the spectral power associated with the PPG waveform and the spectral power not associated with the PPG waveform.

The PPG waveform may then be estimated by summing the time variation of the light reflectivity of each portion of the target multiplied by the weight of the portion of the target as described with respect to, e.g., Step 320 of FIG. 3A.

For example, the time variation of the light reflectivity of the first portion (505) may be multiplied by the weight of the first portion, the time variation of the light reflectivity of the second portion (506) may be multiplied by the weight of the second portion, and the time variation of the light reflectivity of the third portion (507) may be multiplied by the weight of the third portion to form weighted time variations of the light reflectivity of each portion. The weighted time variation of the light reflectivity of each portion may be summed to estimate the PPG waveform.

Example 2

The methods shown in, e.g., FIGS. 3A-E and 4A-B were applied to a patient. Specifically, the methods were applied to the face of a patient. Images of the patient's face were taken over a period of 20 seconds. Associations between pixels of each of the images of the patient were associated with the target using the method shown in, e.g., FIG. 4A.

The face of the patient was subdivided into portions. A weight of each portion and a time variation of the reflectivity of each portion of the face of the patient were determined by the method shown in, e.g., FIG. 3A.

Figure 6:
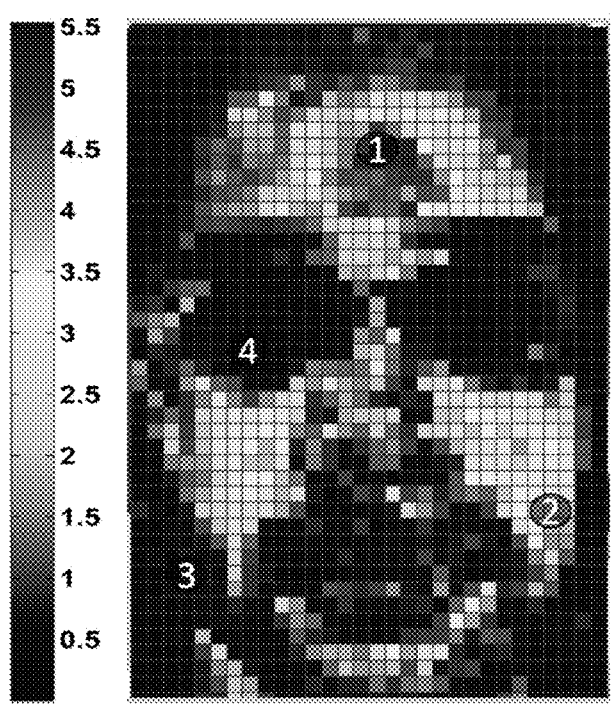
FIG. 6 shows an example diagram illustrating weights of portions of a target in accordance with embodiments of the invention.

FIG. 6 shows a diagram of the weights of each portion of the face of the patient. In FIG. 6, the face of the patient was divided into portions of equal size and lighter colors indicate higher weights. As seen from FIG. 6, there is a large variation of the weight of each portion of the target.

Four markers are superimposed over the diagram shown in FIG. 6 to indicate particular areas of interest. As seen from FIG. 6, markers 1 and 2 are located near portions of the face that are lighter in color thereby indicating higher weight while markers 3 and 4 are located near portions of the face that are darker in color thereby indicating lower weights. Thus, from FIG. 6, it is clear that the time variation of the light reflectivity some portions of the face are more strongly associated with the PPG waveform.

Figure 7:
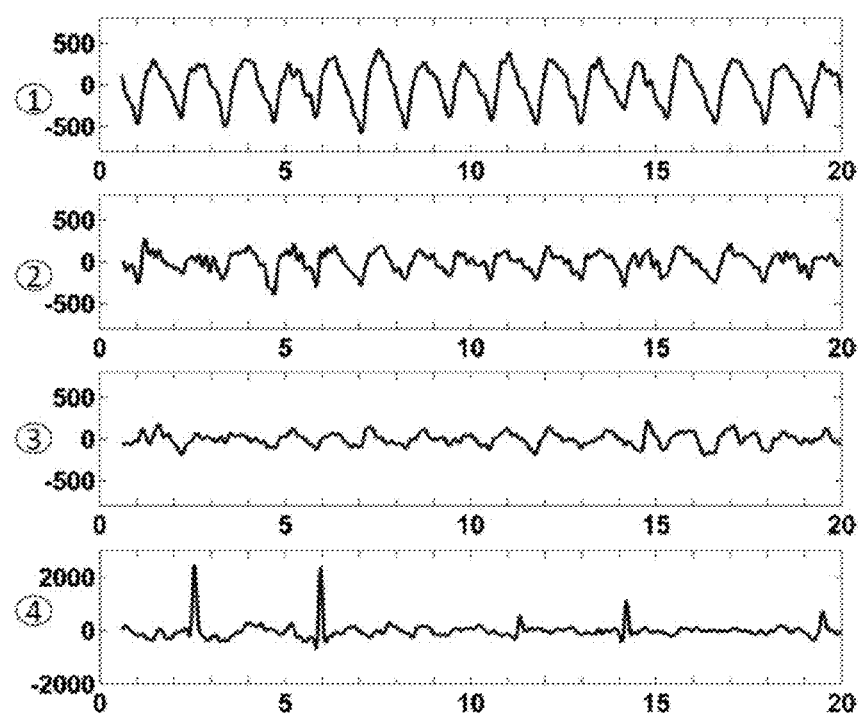
FIG. 7 shows example plots of measured light reflectivity of portions of a target in accordance with embodiments of the invention.

FIG. 7 shows plots of the time variation of the light reflectivity of the portions of the face near markers 1, 2, 3, and 4 of FIG. 6, respectively. In each of the plots, the horizontal axis indicates the time in seconds and the vertical axis indicates the magnitude of the light reflectivity of the portion of the target near the marker.

As seen from the plots associated with the portions near markers 1 and 2, a strong and repetitive signal may be seen within the waveform that may be associated with a PPG waveform of the patient. In contrast, near the markers 3 and 4, it is difficult to visually make out a repetitive signal within the waveform that may be associated with a PPG waveform. Thus, merely averaging the signals near markers 1-4 would not provide a good estimate of a PPG waveform of the patient.

Figure 8:
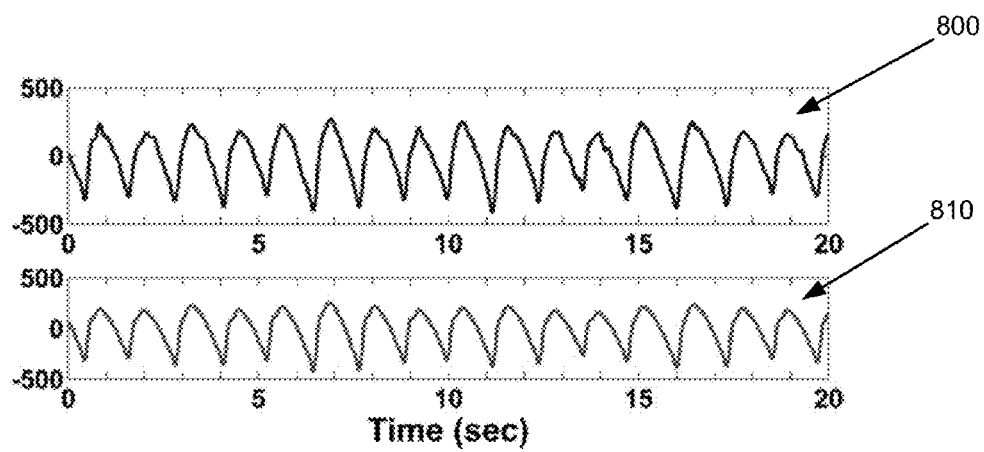
FIG. 8 shows an example plot of an estimated PPG waveform of a target and a measured PPG waveform in accordance with embodiments of the invention.

FIG. 8 shows a first plot (800) of the an estimated PPG waveform based on the weight and time variation of the light intensity of the target and a second plot (810) of the PPG waveform measured using a direct, contact method of measuring the PPG waveform. As seen from FIG. 8, the estimated PPG waveform closely follows the measured PPG waveform and thereby illustrates that the estimated PPG waveforms produced by the methods shown in, e.g., FIGS. 3A-E and 4A-B predict the actual PPG waveform of the patient without requiring direct contact with the patient.

One or more embodiments of the invention may provide one or more of the following advantages: (1) A system or method in accordance with embodiments of the invention may enable areas of a target strongly associated with a PPG waveform to be distinguished from areas of a target weakly or not associated with a PPG waveform, (ii) the system or method may enable a PPG waveform to be estimated without direct contact with a patient and thereby prevent transmission of infections by direct contact methods of measuring a PPG waveform, (iii) the system or method may enable a target within a number of image to be identified and thereby enable pixels of each image to be associated with the target, (iv) the system or method may enable the heart rate and/or the heart rate variability of a target to be determined without contact to the target and thereby be completed without the knowledge of the target, and (v) the determined heart rate and/or the heart rate variability of the target may be used to determine a cognitive stress load of the target, whether the determined heart rate and/or heart rate variability indicate that a statement given by the target is truthful, and the heart rate and/or heart rate variability may be used to facilitate an interrogation of a target by indicating the target's mental state.

While the invention has been described above with respect to a limited number of embodiments, those skilled in the art, having the benefit of this disclosure, will appreciate that other embodiments can be devised which do not depart from the scope of the invention as disclosed herein. Accordingly, the scope of the invention should be limited only by the attached claims.

What is claimed is:

1. A method of estimating a photoplethysmogram (PPG) waveform of a target, comprising:
    obtaining a plurality of images, wherein an image of the plurality of images comprises the target;
    subdividing the target into a plurality of portions;
    determining, based on the plurality of images, a time variation of a light reflectivity of a portion of the plurality of portions;
    determining, based on the time variation of the light reflectivity, a weight associated with the portion of the plurality of portions; and
    estimating the PPG waveform of the target based on the weight and the image of the plurality of images,
    wherein estimating the PPG waveform of the target comprises multiplying the weight of the portion of the plurality of portions by the light reflectivity of the portion of the plurality of portions to form a weighted light reflectivity of the portion.

2. The method of claim 1, wherein obtaining the plurality of images comprises:
    activating an illumination source; and
    capturing a first image of the target while the illumination source is activated.

3. The method of claim 2, wherein obtaining the plurality of images further comprises:
    capturing a second image of the target while the illumination source is activated,
    wherein the second image is captured at a time that is different than a time of capture of the first image.

4. The method of claim 1, wherein determining the time variation of the light reflectivity of the portion of the plurality of portions comprises:
    identifying the target in each image of the plurality of images;
    generating an alignment transformation for each image of the plurality of images based on the location of the target in the image of the plurality of images;
    applying the alignment transform to each image of the plurality of images to associate at least one pixel of each image of the plurality of images with the target; and
    determining the time variation of the light reflectivity of the portion of the plurality of portions based on the at least one pixel of each image of the plurality of each image and a capture time of each image of the plurality of images.

5. The method of claim 1, wherein determining the weight associated with the portion of the plurality of portions comprises:
    generating an estimate of a frequency of the PPG waveform based on the light reflectivity of the portion of plurality of portions;
    determining a first spectral power of the time variation of the light reflectivity of the portion of the plurality of portions in a spectral region including the estimate of the frequency of the PPG waveform;
    determining a second spectral power of the time variation of the light reflectivity of the portion of the plurality of portions in a spectral region that does not include the estimate of the frequency of the PPG waveform; and
    determining the weight based on the first spectral power and the second spectral power.

6. The method of claim 1, further comprising:
    generating an estimate of a frequency of the PPG waveform based on the filtered light reflectivity of the portion of plurality of portions;
    applying a bandpass filter to the filtered time variation of the light reflectivity of the portion of the plurality of portions to generate a filtered time variation of the light reflectivity, wherein a passband of the bandpass filter comprises the estimate of the frequency of the PPG waveform;
    determining a first spectral power of the filtered time variation of the light reflectivity of the portion of the plurality of portions in a spectral region including the estimate of the frequency of the PPG waveform;
    determining a second spectral power of the filtered time variation of the light reflectivity of the portion of the plurality of portions in a spectral region that does not include the estimate of the frequency of the PPG waveform; and
    determining the weight based on the first spectral power and the second spectral power.

7. The method of claim 6, wherein generating an estimate of a frequency of the PPG waveform comprises:
    generating a spectral power density of the filtered time variation of the light reflectivity of the portion of the plurality of portions;
    determining a frequency associated with a maximum of the spectral power density; and
    generating the estimate based on the frequency associated with the maximum of the spectral power density.

8. The method of claim 1, wherein estimating the PPG waveform of the target further comprises:
    multiplying a second weight of a second portion of the plurality of portions by a light reflectivity of the second portion of the plurality of portions to form a weighted light reflectivity of the second portion; and
    summing the weighted light reflectivity of the portion with the weighted light reflectivity of the second portion.

9. A non-transitory computer readable medium (CRM) storing instructions for estimating a photoplethysmogram (PPG) waveform of a target, the instructions comprising functionality for:
    obtaining a plurality of images, wherein an image of the plurality of images comprises the target;
    subdividing the target into a plurality of portions;

determining, based on the plurality of images, a time variation of a light reflectivity of a portion of the plurality of portions;

determining, based on the time variation of the light reflectivity, a weight associated with the portion of the plurality of portions; and estimating the PPG waveform of the target based on the weight and the image of the plurality of images, wherein the instructions for determining the time variation of the light reflectivity of the portion of the plurality of portions comprise functionality for:

identifying the target in each image of the plurality of images;

generating an alignment transformation for each image of the plurality of images based on the location of the target in the image of the plurality of images;

applying the alignment transform to each image of the plurality of images to associate at least one pixel of each image of the plurality of images with the target; and determining the time variation of the light reflectivity of the portion of the plurality of portions based on the at least one pixel of each image of the plurality of each image and a capture time of each image of the plurality of images.

10. The non-transitory CRM of claim 9, wherein the instructions for determining the weight associated with the portion of the plurality of portions comprise functionality for:

generating an estimate of a frequency of the PPG waveform based on the light reflectivity of the portion of plurality of portions;

determining a first spectral power of the time variation of the light reflectivity of the portion of the plurality of portions in a spectral region including the estimate of the frequency of the PPG waveform;

determining a second spectral power of the time variation of the light reflectivity of the portion of the plurality of portions in a spectral region that does not include the estimate of the frequency of the PPG waveform; and determining the weight based on the first spectral power and the second spectral power.

11. A method of estimating a photoplethysmogram (PPG) waveform of a target, comprising:

obtaining a plurality of images, wherein an image of the plurality of images comprises the target;

subdividing the target into a plurality of portions;

determining, based on the plurality of images, a time variation of a light reflectivity of a portion of the plurality of portions;

determining, based on the time variation of the light reflectivity, a weight associated with the portion of the plurality of portions;

estimating the PPG waveform of the target based on the weight and the image of the plurality of images;

generating an estimate of a frequency of the PPG waveform based on the filtered light reflectivity of the portion of plurality of portions;

applying a bandpass filter to the filtered time variation of the light reflectivity of the portion of the plurality of portions to generate a filtered time variation of the light reflectivity, wherein a passband of the bandpass filter comprises the estimate of the frequency of the PPG waveform;

determining a first spectral power of the filtered time variation of the light reflectivity of the portion of the plurality of portions in a spectral region including the estimate of the frequency of the PPG waveform;

determining a second spectral power of the filtered time variation of the light reflectivity of the portion of the plurality of portions in a spectral region that does not include the estimate of the frequency of the PPG waveform; and determining the weight based on the first spectral power and the second spectral power.

12. The method of claim 11, wherein obtaining the plurality of images comprises:

activating an illumination source; and capturing a first image of the target while the illumination source is activated.

13. The method of claim 12, wherein obtaining the plurality of images further comprises:

capturing a second image of the target while the illumination source is activated, wherein the second image is captured at a time that is different than a time of capture of the first image.

14. The method of claim 11, wherein determining the time variation of the light reflectivity of the portion of the plurality of portions comprises:

identifying the target in each image of the plurality of images;

generating an alignment transformation for each image of the plurality of images based on the location of the target in the image of the plurality of images;

applying the alignment transform to each image of the plurality of images to associate at least one pixel of each image of the plurality of images with the target; and determining the time variation of the light reflectivity of the portion of the plurality of portions based on the at least one pixel of each image of the plurality of each image and a capture time of each image of the plurality of images.

15. The method of claim 11, wherein determining the weight associated with the portion of the plurality of portions comprises:

generating an estimate of a frequency of the PPG waveform based on the light reflectivity of the portion of plurality of portions;

determining a first spectral power of the time variation of the light reflectivity of the portion of the plurality of portions in a spectral region including the estimate of the frequency of the PPG waveform;

determining a second spectral power of the time variation of the light reflectivity of the portion of the plurality of portions in a spectral region that does not include the estimate of the frequency of the PPG waveform; and determining the weight based on the first spectral power and the second spectral power.

16. The method of claim 11, wherein generating an estimate of a frequency of the PPG waveform comprises:

generating a spectral power density of the filtered time variation of the light reflectivity of the portion of the plurality of portions;

determining a frequency associated with a maximum of the spectral power density; and generating the estimate based on the frequency associated with the maximum of the spectral power density.

17. The method of claim 11, wherein estimating the PPG waveform of the target comprises:

multiplying the weight the portion of the plurality of portions by the light reflectivity of the portion of the plurality of portions to form a weighted light reflectivity of the first portion.

18. The method of claim 11, wherein estimating the PPG waveform of the target further comprises:
multiplying a second weight of a second portion of the plurality of portions by a light reflectivity of the second portion of the plurality of portions to form a weighted light reflectivity of the second portion; and
summing the weighted light reflectivity of the first portion with the weighted light reflectivity of the second portion.

* * * * *